United States Patent
Krasnobaev et al.

(10) Patent No.: US 6,828,795 B2
(45) Date of Patent: Dec. 7, 2004

(54) EXPLOSIVE DETECTION SYSTEM

(75) Inventors: Leonid Y. Krasnobaev, Newton, MA (US); Vyacheslav S. Persenkov, Moscow (RU); Vladimir V. Belyakov, Lynn, MA (US); Vladimir B. Kekukh, Melrose, MA (US); Stephen N. Bunker, Wakefield, MA (US)

(73) Assignee: Implant Sciences Corporation, Wakefield, MA (US)

( * ) Notice: Subject to any disclaimer, the term of this patent is extended or adjusted under 35 U.S.C. 154(b) by 53 days.

(21) Appl. No.: 10/349,491

(22) Filed: Jan. 22, 2003

(65) Prior Publication Data

US 2003/0193338 A1 Oct. 16, 2003

Related U.S. Application Data

(63) Continuation-in-part of application No. 10/295,010, filed on Nov. 14, 2002, and a continuation-in-part of application No. 10/295,039, filed on Nov. 14, 2002.
(60) Provisional application No. 60/363,485, filed on Mar. 12, 2002, provisional application No. 60/357,618, filed on Feb. 15, 2002, and provisional application No. 60/357,394, filed on Feb. 15, 2002.

(51) Int. Cl.[7] ............................ G11B 5/147; G01N 27/62
(52) U.S. Cl. ...................... 324/464; 340/632; 73/23.35; 73/863.71
(58) Field of Search ........................ 324/464, 468–470; 340/632; 250/286–288; 73/23.35, 23.36, 23.37, 863.71

(56) References Cited

U.S. PATENT DOCUMENTS

| | | | | |
|---|---|---|---|---|
| 5,300,773 A | | 4/1994 | Davies | 250/286 |
| 5,338,931 A | | 8/1994 | Spangler et al. | 250/287 |
| 5,465,607 A | * | 11/1995 | Corrigan et al. | 73/23.36 |
| 5,585,575 A | * | 12/1996 | Corrigan et al. | 73/863.71 |
| 5,728,584 A | | 3/1998 | Sausa et al. | 436/106 |
| 5,759,859 A | | 6/1998 | Sausa | 436/106 |
| 5,826,214 A | | 10/1998 | Lieb et al. | 702/124 |
| 5,834,771 A | * | 11/1998 | Yoon et al. | 250/286 |
| 5,906,946 A | | 5/1999 | Sausa et al. | 436/116 |
| 5,968,837 A | | 10/1999 | Döring et al. | 436/173 |
| 6,239,428 B1 | | 5/2001 | Kunz | 250/287 |
| 6,610,977 B2 | * | 8/2003 | Megerle | 250/287 |

* cited by examiner

Primary Examiner—Vincent Q. Nguyen
(74) Attorney, Agent, or Firm—Choate, Hall & Stewart

(57) ABSTRACT

An explosive detection system detects the presence of trace molecules in air. The sensitivity of such instruments is dependent on the concentration of target gas in the sample. The sampling efficiency can be greatly improved when the target object is warmed, even by only a few degrees. A directed emission of photons, typically infrared or visible light, can be used to significantly enhance vapor emission. The sensitivity of such instruments is also dependent on the method of gas sampling utilized. A cyclone sampling nozzle can greatly improve the sampling efficiency, particularly when the sampling needs to be performed at a distance from the air intake.

43 Claims, 5 Drawing Sheets

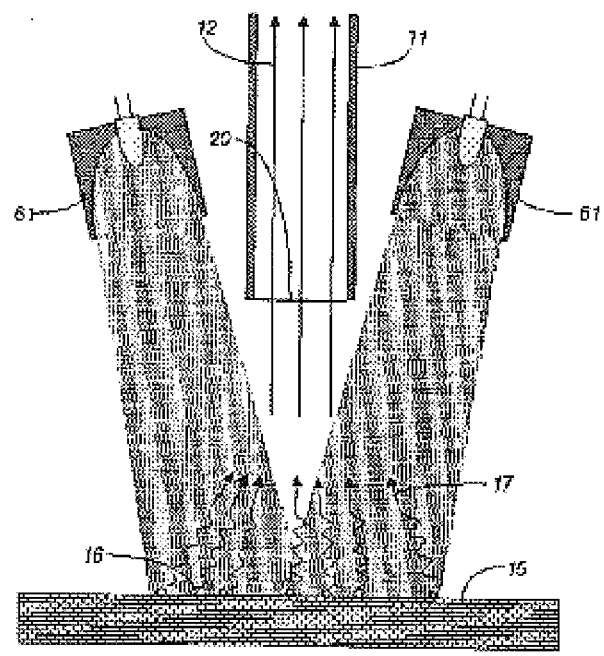
FIG. 3
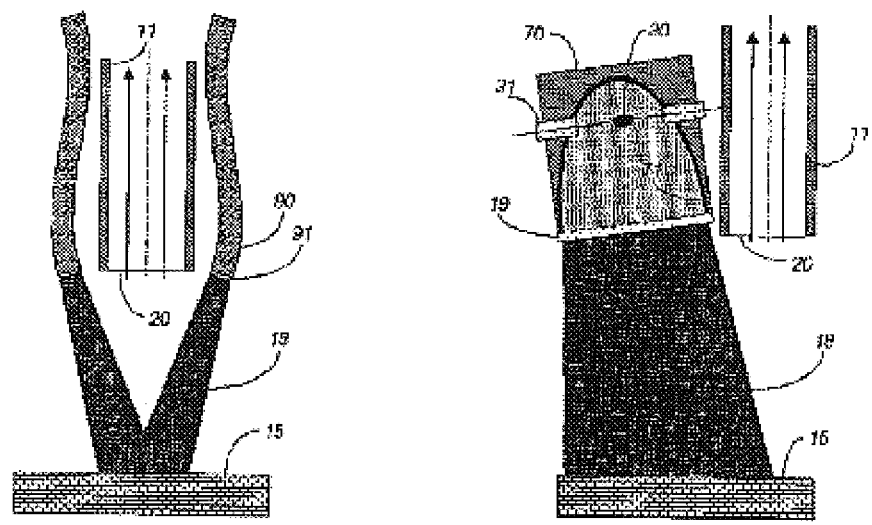
FIG. 4A
FIG. 4B

EXPLOSIVE DETECTION SYSTEM

CROSS-REFERENCE TO RELATED APPLICATIONS

This application is a continuation-in-part of U.S. patent application Ser. No. 10/295,010, filed on Nov. 14, 2002 (pending), and U.S. patent application Ser. No. 10/295,039, filed on Nov. 14, 2002 (pending), and claims benefit and priority from U.S. Provisional Application No. 60/357,394, filed Feb. 15, 2002, U.S. Provisional Application No. 60/357,618, filed Feb. 15, 2002, and U.S. Provisional Application No. 60/363,485, filed Mar. 12, 2002, all of which are incorporated herein by reference.

BACKGROUND OF THE INVENTION

1. Field of the Invention

This invention relates to detection of explosives and more particularly to an ion mobility spectrometry instrument that detects chemicals present as vapors in air or other gases, or liberated as vapors from condensed phases such as particles or solutions.

2. Description of Related Art

IMS instruments operate on the basis of the time taken by ionized molecules to move through a gas-filled drift region to a current collector while under the influence of an electric field. The ions are created in a gas-filled region called the ion source, which is connected to the drift region through an orifice or a barrier grid. The ion source may use any of a variety of techniques to ionize atoms and molecules. One or more flowing streams of gas enter the ion source through one or more orifices, and the gas may exit through one or more different orifices. At least one of the flowing gas streams entering the ion source includes gas that has been sampled (the "sample gas") from the surrounding atmosphere or other source of vapor to be analyzed.

In same cases, the process of taking a sample begins with an operator rubbing an absorbent substance, such as chemical filter paper, onto the surface to be tested. Particles of the chemical of interest may then be transferred and concentrated on the absorber. This intermediate absorber is then brought to the vicinity of the sampling orifice of the IMS. The method of concentrating using an absorbent substance is deficient in that it tends to be relatively slow to implement and is subject to variations in the skill of the operator. Additionally, while the absorber is relatively low in cost, the process of taking a great many samples becomes expensive in that the absorber generally should only be used once to ensure consistent results.

The quantity of particles of the target substance on the target surface is usually very small, often corresponding to only nanograms or even picograms of particles per square centimeter. The IMS must be very sensitive to identify a positive signal from evaporated target molecules when the initial concentration and surface area of target particles is so small.

A sampling method that is employed is to provide a gas pump, which draws the sample gas into the ion source through a tube. For example, the pump may be disposed to provide a partial vacuum at the exit of the ion source. The partial vacuum is transmitted through the confines of the ion source and appears at the entrance orifice of the ion source. A further tubulation may be provided as an extension to a more conveniently disposed sampling orifice external to the IMS. The operator places a sample in the near vicinity of this external sampling orifice, and the ambient vapor is drawn into the gas flow moving towards the ion source.

The ion source of the IMS provides a signal that is approximately proportional to the concentration of target molecule vapor. This concentration is further dependent on the equilibrium vapor pressure of the target molecule, the temperature of the target molecule where it is emitting the vapor, the total flow rate of non-target gas that dilutes the target vapor, and possible adsorption losses on surfaces of the gas sampling system. Existing systems that utilize absorbent surface concentration sometimes employ an oven to greatly warm the absorbent material, often up to 200°, and thereby increase the target vapor concentration.

In some circumstances, it is desirable for IMS instruments to be able to sample vapors at a distance from the external sampling orifice. Examples may include, but not be limited to, sampling of vapor from complex surfaces that contain many holes, crevices, or deep depressions, textured materials such as cloth, people and animals that prefer not to be rubbed by absorbent material, large three dimensional objects, surfaces that must be sampled in a short time, and surfaces in which surface rubbing by human operators is inconvenient or expensive. In addition, it has been observed that the sampling orifice may become contaminated with vapor-emitting particles if the sample inadvertently contacts the orifice. Such contamination is particularly difficult to remove in a short period of time, thus preventing continuous operation of the instrument. Such contamination could be avoided if vapors are sampled at a distance from the sampling orifice.

The distance where vapors may be sampled beyond the sampling orifice may be increased by increasing the sample gas flow rate, i.e., increasing the pumping speed. However, besides the interference with the performance of the ion source of the IMS caused by high velocity flow, this method dilutes the concentration of the desired sample vapor by mixing in a much larger volume of ambient gas. Therefore, the sensitivity of the IMS may decline if the sample gas flow rate is increased excessively.

Warming surfaces at a distance using an oven is generally not very efficient. While warmed gas can be blown onto a distant surface, for example with a "heat gun", when the target surface is a living person or animal, this may not be an acceptable option. Additionally, many surfaces cannot tolerate excessive heating and may be damaged.

SUMMARY OF THE INVENTION

According to the present invention, an explosive detection system includes a sampling orifice that receives sampled gas, a fluid rotator that creates a cyclonic gas flow beyond the sampling orifice, an ion source, coupled to the sampling orifice, that generates ions corresponding to the sampled gas, a drift tube having the ion source coupled to a first end thereof, and a detector coupled to an other end of the drift tube, where the detector detects in the sampled gas the presence of ions associated with explosives. The cyclonic gas flow may have an outer rotary flow about an axis substantially parallel to the central axis of the sampling orifice and an inner flow substantially parallel to the central axis of the sampling orifice. The drift tube may operate at substantially ambient gas pressure. A gas pump may draw a gas flow through the sampling orifice and generate a vacuum within 50 millimeters of mercury (50 Torr) of the substantially ambient gas pressure. The fluid rotator may include at least one vane. The fluid rotator may include a rotation-inducing orifice surrounding the sampling orifice. The inside surface of the rotation-inducing orifice may deflect a gas flow into a cyclonic gas flow. The explosive detection system may further include a gas pump connected to the rotation-inducing orifice that creates a cyclonic gas flow. The explosive detection system may include a precipitator that removes at least a portion of any entrained particles within the gas flow into the sampling orifice. The precipitator may be an electrostatic precipitator. The electrostatic precipitator may include a cathode disposed on or near the drift tube, the cathode applying a voltage greater than 3000 Volts. The axis of the cyclonic gas flow may rotate about a rotation axis perpendicular to its central axis. The axis of the cyclonic gas flow may rotate about a plurality of rotation axes perpendicular to its central axis.

According further to the present invention, an explosive detection system includes a sampling inlet that receives sampled gas, a heat source, mounted proximal to the gas sampling inlet, the heat source providing photonic emissions to one side of a target proximal to the sampling inlet, an ion source, coupled to the sampling orifice, that generates ions corresponding to the sampled gas, a drift tube having the ion source coupled to a first end thereof, and a detector coupled to an other end of the drift tube, where the detector detects in the sampled gas the presence of ions associated with explosives. The photonic emissions may be substantially in the infrared portion of the spectrum. The source of photon emission may be made to be substantially in the infrared using at least one of a filter, coating, and covering. The source of photon emission may have enhanced emission substantially in the infrared by means of conversion of visible light photons to infrared photons. The photonic emissions may be substantially in the combined visible and infrared portion of the spectrum. The photonic emissions may be substantially in the visible portion of the spectrum. The source of photon emission may be made to be substantially in the visible using at least one of a filter, coating, and covering. The photonic emissions may be provided by at least one of a thermally heated surface, a laser, a light emitting diode, and an electrical discharge in a gas. The source of photon emission may be at least one of: pulsed, keyed in a long pulse, and continuous. The source of photon emission may be separated from the target surface by at least one of a window and a semi-transparent grid.

According further to the present invention, a target sample heating system for an ion mobility spectrometer includes a source of photon emission substantially in the infrared portion of the spectrum, means for concentrating the photon emission into a beam, and means for guiding the photon emission towards a target surface. The source of photon emission may be at least one of: a thermally heated surface, laser, light emitting diode, and an electrical discharge in a gas. The source of photon emission may be at least one of: pulsed, keyed in a long pulse, and continuous. The means for concentrating the photon emission may be at least one of a mirror, lens, and fiber optic wave guide. The means for guiding the photon emission towards a target surface may be at least one of a mirror, lens, and fiber optic wave guide. The means for guiding the photon emission may be moved or tilted while guiding the photon emission. The source of photon emission may be made to be substantially in the infrared using at least one of a filter, coating, and covering. The source of photon emission may have enhanced emission substantially in the infrared by means of conversion of visible light photons to infrared photons. The source of photon emission may be separated from the target surface by at least one of a window and a semi-transparent grid.

According further to the present invention, a target sample heating system for an ion mobility spectrometer includes a source of photon emission substantially in the combined visible and infrared portion of the spectrum, means for concentrating the photon emission into a beam, and means for guiding the photon emission towards a target surface. The source of photon emission may be at least one of a thermally heated surface, a laser, light emitting diode, and an electrical discharge in a gas. The source of photon emission may be at least one of: pulsed, keyed in a long pulse, and continuous. The means for concentrating the photon emission may be at least one of a mirror, lens, and fiber optic wave guide. The means for guiding the photon emission towards a target surface may be at least one of a mirror, lens, and fiber optic wave guide. The means for guiding the photon emission may be moved or tilted while guiding the photon emission. The source of photon emission may be separated from the target surface by at least one of a window and a semi-transparent grid.

According further to the present invention, a target sample heating system for an ion mobility spectrometer includes a source of photon emission substantially in the visible portion of the spectrum, means for concentrating the photon emission into a beam, and means for guiding the photon emission towards a target surface. The source of photon emission may be at least one of a thermally heated surface, a laser, light emitting diode, and an electrical discharge in a gas. The source of photon emission may be at least one of: pulsed, keyed in a long pulse, and continuous. The means for concentrating the photon emission may be at least one of mirror, lens, and fiber optic wave guide. The means for guiding the photon emission towards a target surface may be at least one of a mirror, lens, and fiber optic wave guide. The means for guiding the photon emission may be moved or tilted while guiding the photon emission. The source of photon emission may be made to be substantially in the visible using at least one of a filter, coating, and covering. The source of photon emission may be separated from the target surface by at least one of a window and a semi-transparent grid.

According further to the present invention, a sampling system for an IMS includes a gas sampling inlet that samples vapors from a target and provides the vapors to the IMS and a heat source, mounted proximal to the gas sampling inlet, the heat source providing photonic emissions to the target in connection with the inlet sampling vapors. The photonic emissions may be substantially in the infrared portion of the spectrum. The source of photon emission may be made to be substantially in the infrared using at least one of a filter, coating, and covering. The source of photon emission may have enhanced emission substantially in the infrared by means of conversion of visible light photons to infrared photons. The photonic emissions may be substantially in the combined visible and infrared portion of the spectrum. The photonic emissions may be substantially in the visible portion of the spectrum. The source of photon emission may be made to be substantially in the visible using at least one of a filter, coating, and covering. The photonic emissions may be provided by at least one of a thermally heated surface, a laser, a light emitting diode, and an electrical discharge in a gas. The source of photon emission may be at least one of: pulsed, keyed in a long pulse, and continuous. The source of photon emission may be separated from the target surface by at least one of a window and a semi-transparent grid.

According further to the present invention, a gas sampling system for an ion mobility spectrometer includes a first gas pump providing a gas flow at a partial gas vacuum compared to ambient gas pressure, a second gas pump providing a gas flow at a partial gas pressure compared to the ambient gas pressure, a first orifice for the partial gas vacuum which is external to the ion mobility spectrometer, tubulation means connecting the first orifice to the ion mobility spectrometer, a second orifice for the partial gas pressure which is concentric and external to the first orifice, and gas deflection means for inducing a rotational cyclonic motion of the gas flow from the second orifice. The partial gas vacuum may be within 50 millimeters of mercury (50 Torr) of the ambient gas pressure. The partial gas pressure may be within 50 millimeters of mercury (50 Torr) of the ambient gas pressure. The gas deflection may be provided by vanes or by the inside surface of the second orifice.

According further to the present invention, a gas sampling system for an ion mobility spectrometer includes a first gas pump providing a gas flow at a partial gas vacuum compared to ambient gas pressure, a second gas pump providing a gas flow at a partial gas pressure compared to the ambient gas pressure, a first orifice for the partial gas vacuum which is external to the ion mobility spectrometer, tubulation means connecting the first orifice to the ion mobility spectrometer, a second orifice for the partial gas pressure which is concentric and external to the first orifice, gas deflection means for inducing a rotational cyclonic motion of the gas flow from the second orifice; and electrostatic field means for precipitating particles inside the tubulation means. The partial gas vacuum may be within 50 millimeters of mercury (50 Torr) of the ambient gas pressure. The partial gas pressure may be within 50 millimeters of mercury (50 Torr) of the ambient gas pressure. Gas deflection may be provided by vanes or by the inside surface of the second orifice. The electrostatic means may be provided by a cathode disposed substantially on the axis of the tubulation with an applied voltage greater than 3000 Volts.

According further to the present invention, a gas sampling system includes an ion mobility spectrometer having a sampling orifice and a fluid rotator that creates a cyclonic gas flow beyond the sampling orifice, the cyclonic gas flow having an outer rotary flow about an axis substantially parallel to the central axis of the sampling orifice and an inner flow substantially parallel to the central axis of the sampling orifice. The ion mobility spectrometer may operate at substantially ambient gas pressure. A gas pump may draw a gas flow through the sampling orifice and generate a vacuum within 50 millimeters of mercury (50 Torr) of the substantially ambient gas pressure. The fluid rotator may include at least one vane. The fluid rotator may include a rotation-inducing orifice surrounding the sampling orifice. The inside surface of the rotation-inducing orifice may deflect a gas flow into a cyclonic gas flow. The gas sampling system may also include a gas pump connected to the rotation-inducing orifice that creates a cyclonic gas flow. The gas sampling system may also include a precipitator that removes at least a portion of any entrained particles within the gas flow into the sampling orifice. The precipitator may be an electrostatic precipitator. The electrostatic precipitator may include a cathode disposed on or near the drift tube, the cathode applying a voltage greater than 3000 Volts. The axis of the cyclonic gas flow may rotate about a rotation axis perpendicular to its central axis. The axis of the cyclonic gas flow may rotate about a plurality of rotation axes perpendicular to its central axis.

According further to the present invention, a compound gas sampling system for an ion mobility spectrometer, includes a plurality of gas sampling systems as described herein, the gas sampling systems arranged so that adjacent cyclonic flows rotate in opposing directions.

The invention applies to an ion mobility spectrometer that uses an external sampling orifice to draw in vapors to be analyzed. A method for warming a distant target surface is described using at least one of several techniques. The goal is to heat the target surface in a manner such that the action of heating is unobtrusive, perhaps invisible, the sampled portion of the surface is warmed at least 5° C., and only the surface is warmed, not the bulk of the target material. These conditions may be accomplished using one or more infrared light sources, one or more visible light sources, or a mixture of the two. A light source that is substantially in the infrared portion of the spectrum has the advantage that it is largely invisible to the eye, except for a slight reddish appearance. However, brighter light sources, that warm the surface more quickly, can be produced more easily using visible light. Infrared wavelengths are generally considered to be longer than 700 nanometers and shorter than 100 micrometers. Visible wavelengths are generally considered to be in the range of 700 nanometers to 300 nanometers. Most sources of visible light produce some small percentage of ultraviolet light less than 300 nanometers and some small percentage of infrared light. Most light sources, except lasers, produce broad distributions of wavelengths, and a source is considered to be a visible light source if the peak of its distribution is in the visible range of wavelengths.

It is preferable to utilize means for guiding and concentrating the photon beam from the light source towards the place on the target surface where gas sampling is most efficiently being performed in order to minimize the power consumption, heat primarily the target surface of interest, and maximize the lifetime of the light source. The means may be in the form of one or more lenses, one or more mirrors, fiber optic cable, or some combination of these. An example would consist of a parabolic mirror combined with a nearly point source of infrared light. With the point source situated near to the focal point of the mirror, a substantially parallel infrared beam results, which can then be directed at the desired location on the target surface.

The source of light may be continuous or pulsed. Pulsed light has the advantage of conserving energy and avoiding overheating of the target surface. A desirable feature is to turn off the light source when not in use, but a continuous output light source often requires time to come to stable operating conditions. An alternate embodiment would be to combine a shutter with the continuous output light source in order to simulate a pulsed source. Equivalently, the source of light may be pulsed with a long duration on the order of seconds, sometimes referred to as "keyed".

The interaction of the light radiation with the particles of target material depends on the wavelength of radiation employed. At some wavelengths, the target particles may substantially reflect the incident radiation, thus not absorbing energy and becoming warmed. Heating is then accomplished indirectly by using the incident radiation to warm the surface on which the target particles are attached with heat being transferred to the target particles by conduction, convection, or conversion of the incident wavelength to one that is substantially longer where the target molecules are more absorptive.

There are many well-known sources of infrared and visible light that may be utilized. A hot wire, possible heated electrically, may be used for infrared emission. The wire temperature may be near 800° C. to 850° C. when operated in air. An example of a pulsed visible light source is a xenon flash lamp, in which the pulse duration in one embodiment is approximately $10^{-4}$ seconds. Laser light sources are available both pulsed and continuous at single wavelengths covering much of the infrared and visible light spectrum.

The invention applies to an ion mobility spectrometer that uses an external sampling orifice to draw in vapors to be analyzed. In addition to this existing orifice, a coaxial orifice is provided which emits gas towards the object to be sampled. The emitted gas is further deflected such that it is induced to move in a circular flow about the axis of the external sampling orifice. A further component of the motion is a net velocity away from the external sampling orifice. This type of flow is often referred to as a cyclone. The spinning motion results in a radially-outward directed centrifugal force that restrains the emitted gas flow from immediately being drawn radially inward into the partial vacuum of the external sampling orifice. Eventually, friction with the surrounding ambient gas will slow the emitted gas sufficiently that it will be drawn into the partial vacuum at some distance from the external sampling orifice. Depending on the flow of the emitted gas, this distance can be varied from near the external sampling orifice (low flow) to far from the external sampling orifice (high flow). The cyclonic motion in effect creates a tube consisting of a wall of moving gas that behaves like an extension of the tube that formed the external sampling orifice.

BRIEF DESCRIPTION OF THE DRAWING

The invention is described with reference to the several figures of the drawing, in which.

FIG. 3 shows a possible embodiment showing the focused light beams from a pair of pulsed visible light parabolic reflection modules aimed at a common location in front of the gas sampling orifice of the IMS.

FIG. 4A is a schematic showing a possible embodiment for transmission of the photon beam using fiber optic light guides.

FIG. 4B is a schematic showing a possible embodiment for filtering of the photon beam using a cold mirror.

DETAILED DESCRIPTION

Figure 1:
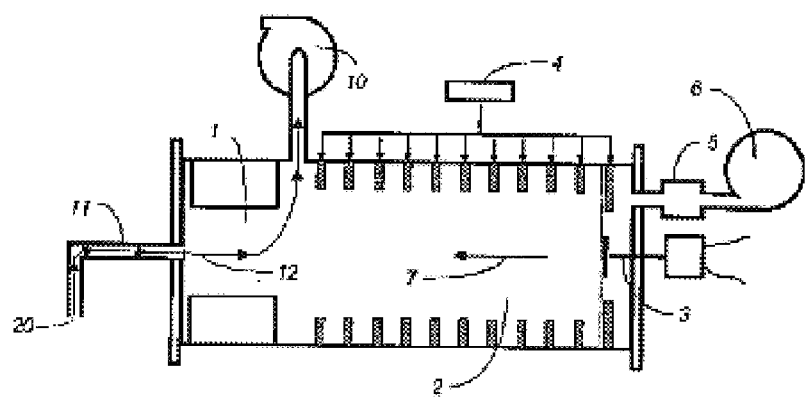
FIG. 1 is a schematic of an IMS detector that may be used in connection with the system disclosed herein.

An explosive detection system that uses an IMS is illustrated in FIG. 1. While various embodiments may differ in details, FIG. 1 shows basic features of an explosive detection system that may be used in connection with the system described herein. The explosive detection system includes an ion source 1, a drift tube 2, a current collector 3, a source of operating voltage 4 and a source of purified drift gas 5, possibly with it own gas pump 6. An explosive detection system may already include a gas pump for gas sampling 10 and a tubular connection 11 between the ion source 1 and an external gas sampling inlet 20 that includes an orifice. Gas flow for the drift gas 7 moves through the drift tube 2. Sampling gas flow 12 moves from the external gas sampling inlet 20 through the tubular connection 11 and ion source 1 to the gas sampling pump 10.

In practice, the explosive detection system of FIG. 1 may be used to sample gas proximal to different areas of a person without having any part of the explosive detection system touch the person. The explosive detection system of FIG. 1 may also be used to sample gas proximal to packages, luggage, etc. As described herein, features of the explosive detection system facilitate detection of chemicals associated with explosives in an unobtrusive manner.

Conventional ion spectrometer systems may use an oven-like chamber that heats the target on all sides. In contrast, the system described herein uses various types of lamps and/or radiative elements to project radiation that heats one side of the target. Heating one side of the target provides advantages over the conventional oven-type systems, including eliminating the inconvenience of having to place the entire target in a chamber that is heated.

Figure 2A:
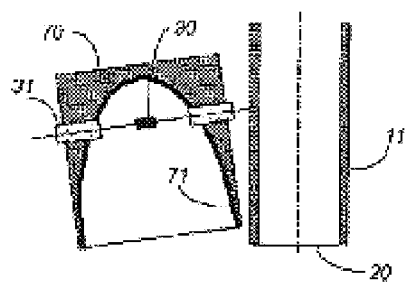
FIG. 2A is a schematic diagram showing a possible embodiment for a radiative target sample heating unit that uses an electrically heated coil of wire at the focus of a parabolic reflector.

FIGS. 2A–2D show a selection of possible embodiments for a radiative heating element, provided proximal to the gas sampling inlet 20, that heats the target surface in conjunction with the gas sampling system of the explosive detection system. In FIG. 2A, the technique for heating combines a continuous electrically heated wire 30, which emits substantially in the infrared, with a parabolic reflector 70. The coil of heated wire is disposed at or near the focal point of the reflector in order to form a beam of photons that is substantially parallel. The electrically heated wire 30 (e.g., a coil) may also be disposed slightly offset of the focal point of the reflector in order to form a beam cross section that is either slightly converging or diverging, depending on the target area of interest. The electrically heated wire 30 is electrically insulated from the reflector 70 by means of insulators 31. The reflector 70 may optionally be polished and optionally coated with a reflective material 71. The electrically heated wire may also be optionally disposed within a sealed enclosure, such as an evacuated transparent glass bulb.

Figure 2C:
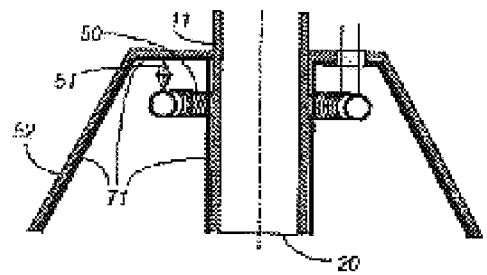
FIG. 2C is a schematic diagram showing a possible embodiment for a radiative target sample heating unit that uses a toroidal heated coil of wire within a component of a gas cyclone used in gas sampling.
Figure 2B:
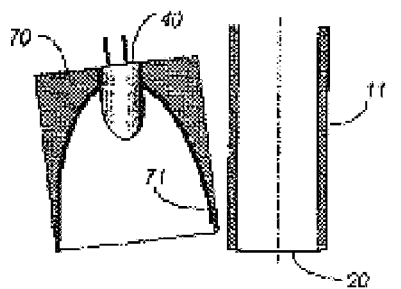
FIG. 2B is a schematic diagram showing a possible embodiment for a radiative target sample heating unit that uses a pulsed visible light lamp near the focus of a parabolic reflector.
Figure 2D:
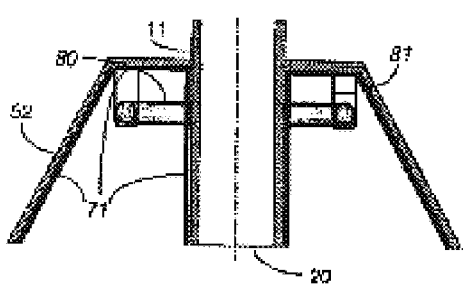
FIG. 2D is a schematic diagram showing a possible embodiment for a radiative target sample heating unit that uses a pulsed visible light lamp within a component of a gas cyclone used in gas sampling.

In FIG. 2B, the light source is provided by a miniature pulsed xenon gas-filled lamp 40. A parabolic reflector 70 is shown with a coating of a reflective material 71. In FIG. 2C, a conical reflector 52 is employed which may also be a component of the gas sampling system of the explosive detection system, such as a cyclone nozzle. The infrared radiation is produced by a toroidally-shaped coil of electrically heated wire 50, which is mounted on insulators 51. In FIG. 2D, the reflector is similar to that for FIG. 2C, but the light is provided by a toroidally-shaped pulsed xenon lamp 80 mounted on wires 81.

FIG. 3 shows a possible embodiment in the form of two pulsed visible light lamp modules 61 mounted proximal to the tubular connection 11 to the explosive detection system and to the gas sampling inlet 20. The lamp modules 61 focus their photon beams 18 onto the target surface 15, heating target particles 16 and causing the enhanced emission of target molecule vapors 17. The target molecule vapors 17 are entrained in the gas flow 12 entering the gas sampling inlet 20. Different numbers of the same or different types of heating modules may be used.

Light sources that produce a spectrum of wavelengths substantially in the visible band may optionally be coated, filtered, or covered with infrared-enhancing materials in order to increase the infrared fraction of the output spectrum. Such materials may act as transmission filters in which the infrared component is selectively passed, or they may alternatively convert a portion of the incident visible light photons to infrared photons, possibly by heating a secondary surface to a high temperature. Similarly, evacuated glass bulbs that have output primarily in visible light may have surface coatings, internal gases, or filters to increase the infrared fraction of the output spectrum. The filter, coating, or covering may optionally be in the form of a mirror that selectively reflects infrared, commonly called a "hot mirror". Alternatively, the filter, coating, or covering may be a "cold mirror" that reflects visible but transmits infrared, particularly as a protective window. Such protective windows are useful for isolating hot or delicate sources of light radiation. In addition to a cold mirror, a transparent window or open mesh grid may also be used as a protective window.

FIGS. 4A and 4B show other possible embodiments for transmitting the photon beam or beams to the target surface 15. In FIG. 4A, fiber optic light guides 90 are disposed proximal to the tubular connection 11 to the explosive detection system and to the gas sampling inlet 20. In the embodiment shown, a lens 91 is employed to minimize the divergence of the photon beam 18 being emitted by the fiber optic cable 90. The photon beams 18 are aimed at positions on the target surface 15 to enhance the emission of target molecule vapor. The positions may optionally be selected to overlap and reinforce one another or to illuminate separate locations. In FIG. 4B, a cold mirror 19 may be employed together with the light module of FIG. 2A in order to enhance the infrared fraction of the photon beam 18.

Fiber optics or similar light guides may be used to separate the location of light generation and the illumination of the target surface to permit physically larger lamps than would be possible nearer to the sampling inlet 20. Moving mirrors may be used to scan the infrared or visible optical beam in order to define a larger irradiated surface area. A variable focus lens or the position of the optical source relative to the mirror may be utilized to change the optical beam cross section or to selectively focus the optical beam at a particular distance.

Figure 5:
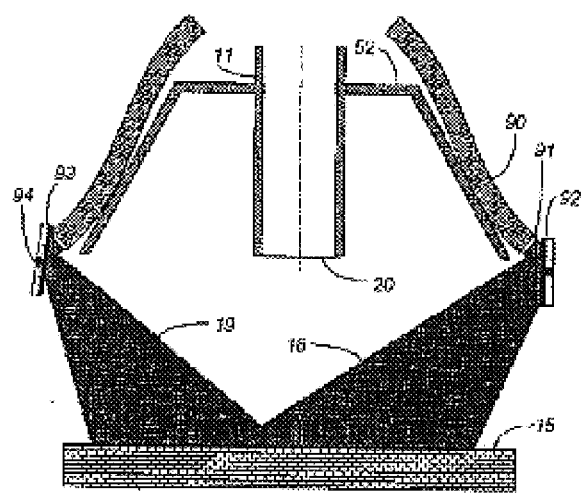
FIG. 5 is a schematic showing a possible embodiment for scanning the photon beam or beams using one or more moving hot mirrors.

FIG. 5 show a possible embodiment for transmitting the photon beam or beams to the target surface 15 when a conical nozzle 52 for a cyclone is employed, such as the disclosed in U.S. provisional patent application 60/357,394. In this embodiment, hot mirrors 93 reflect the photon beam 18 emitted from fiber optic cables 90. A lens 91 is employed to focus the photon beam 18, although in an alternate embodiment the hot mirror 93 could have a concave surface to accomplish similar focusing control. The hot mirrors 93 may also be optionally tilted about axis 94 in order to scan the photon beam 18 across the target surface 15.

Other methods of optical emission, transmission, filtering, and focusing are possible, and the specifically described embodiments should not be understood as restricting the scope of the invention.

When operating conventional IMS systems, increasing the sample gas flow rate increases the volume of gas sampled in a given amount of time, which can result in more sensitive detection. However, a higher sample gas flow rate also increases the velocity of the gas through the ion source, and too high a velocity can interfere with the performance of the IMS. In addition, a sampling orifice having the general form consisting of the end of a hollow tube will draw gas from locations disposed both directly in front of the orifice as well as locations disposed to the side of the orifice. The partial vacuum supplied by the gas pump declines rapidly to ambient gas pressure within a short distance from the sampling orifice, because gas is flowing into the orifice from many directions.

In some circumstances, such as explosive detection, it is desirable for IMS instruments to be able to sample vapors at a distance from the external sampling orifice. Examples may include, but are not limited to, sampling of vapor from complex surfaces that contain many holes, crevices, or deep depressions, people and animals that prefer not to be rubbed by absorbent material, large three dimensional objects, textured materials such as cloth, surfaces that must be sampled in a short time, and surfaces in which surface rubbing by human operators is inconvenient or expensive.

In addition, the sampling orifice may become contaminated with vapor-emitting particles if the sample inadvertently contacts the orifice. Such contamination is particularly difficult to remove in a short period of time, thus preventing continuous operation of the instrument. Such contamination could be avoided if vapors could be sampled at a distance from the sampling orifice, but sampling from a distance tends to substantially dilute the sampled gas and thus to reduce sensitivity.

The distance where vapors may be sampled beyond the sampling orifice may be increased by increasing the sample gas flow rate, i.e., increasing the pumping speed. However, besides the interference with the performance of the ion source of the IMS caused by high velocity flow, this method dilutes the concentration of the desired sample vapor by mixing in a much larger volume of ambient gas. Therefore, the sensitivity of the IMS may decline if the sample gas flow rate is increased excessively.

The sampling of vapors with the ordinary sampling orifice is not highly directional. This is normally of little consequence in conventional detectors, since the volume being sampled must normally be disposed very near to the orifice, and directionality is provided by moving the orifice to another location.

Figures 6A, 6B, 6C:
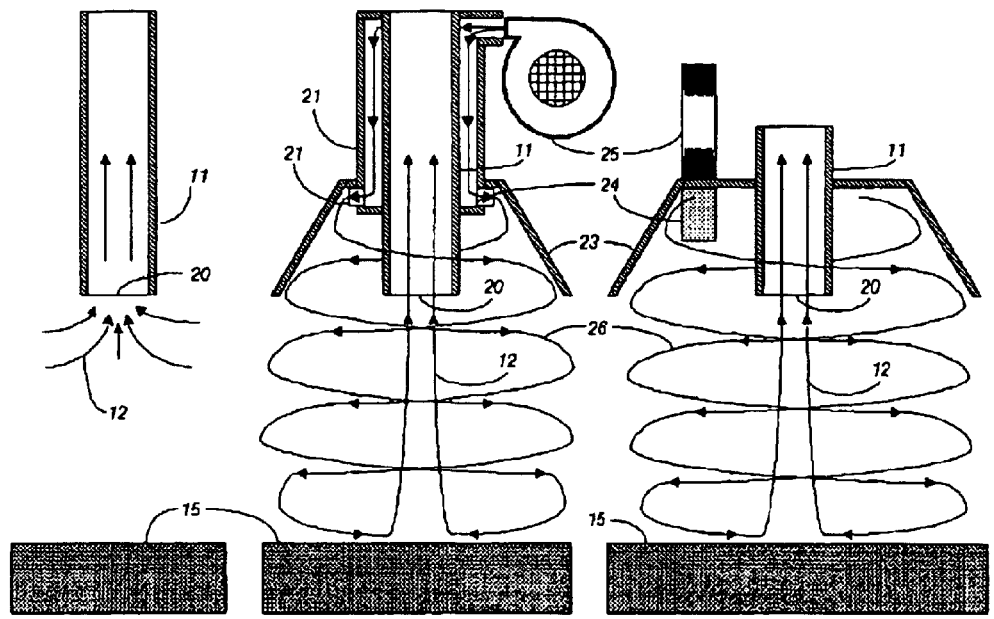
FIG. 6A is a schematic showing gas flow in a conventional gas sampling system not using a cyclonic flow.
FIG. 6B is a schematic showing a cyclone gas sampling system with a cone-shaped nozzle using deflection vanes.
FIG. 6C is a schematic showing a cyclone gas sampling system with a cone-shaped nozzle using tangential gas flow.

For purposes of comparison, a conventional gas sampling system is shown in FIG. 6A. The gas pump for vacuum 10 may be disposed elsewhere and is not shown in the figure. The portion of the tubular connection 11 nearest the external gas sampling orifice 20 is shown. The sampling gas flow 12 shows that the volume of gas being sampled is disposed near to the external gas sampling orifice 20, and gas is being drawn into the orifice 20 over an angular range between substantially perpendicular to the axis of the orifice to on the axis of the orifice 20. When a target surface 15 is disposed at a distance greater than 1–2 times the diameter of the external gas sampling orifice 20, the quantity of sampled gas is either very small or highly diluted by the more abundant gas sampled from nearer the external gas sampling orifice 20.

A cyclone gas sampling system includes the following components as shown in FIGS. 6B and 6C. A partial vacuum relative to ambient gas pressure is supplied by a gas pump (not shown). The gas pump may be disposed at some distance from the cyclone gas sampling system with the vacuum being guided to the cyclone gas sampling system by means of a tubulation or conduit 11. The gas pump and corresponding tubulation 11 may already be part of an existing IMS. A partial pressure relative to ambient gas pressure is supplied by a gas pump 25. The gas pump 25 may be disposed at some distance from the cyclone gas sampling system with the pressure being guided to the cyclone gas sampling system by means of a tubulation or conduit 21. It is preferable that the pressure gas pump is separate from the vacuum gas pump to avoid cross-contamination of the sample gas between the two gas flows. The pressure gas flow 26 is induced to move in a circular, cyclonic motion away from the cyclone gas sampling system by a fluid rotator. The fluid rotator may include, for example, gas deflection vanes (shown in FIG. 6B), or a hollow, cylindrically or conically shaped orifice 23 concentric with the orifice for the partial vacuum 20. An alternate embodiment is to introduce the pressure gas flow through an orifice 24, which is oriented tangential to the hollow cylindrically or conically shaped orifice 23 and is deflected into a circular flow by means of the curvature of the inside wall. The pressure gas flow orifice 24 may be singular or a plurality of such orifices. The gas pump 25 may also be singular or a plurality of such pumps. Other means for inducing rotary flow of a gas, such as a turbine, are known in the art and are also included within the scope of the invention.

Figure 7:
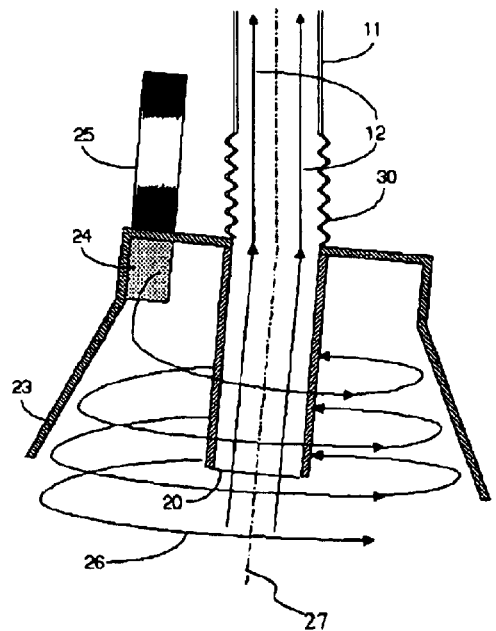
FIG. 7 shows a plurality of cyclones arranged in a rectilinear grid.

The axis of the emitted cyclonic gas flow defines the axis for guiding the partial vacuum from the external sampling orifice. If the axis of the emitted cyclonic flow is tilted over a small angular range, the partial vacuum due to the flow at the external sampling orifice follows this tilting motion, effectively scanning the position of the virtual gas sampling location. This characteristic is useful for sampling over a one dimensional stripe or a two dimensional surface area without moving the IMS (explosive detection system) from a fixed location. FIG. 7 shows one possible embodiment of a tilted cyclone in which the gas sampling tubulation 11 is flexible. Other possible embodiments would include, but not be limited to a ball joint within tubulation 11, a tilting cylindrical or conical surface 23 with the tubulation 11 fixed, and dynamic control of the relative velocities of a plurality of gas flows 26. As an alternative embodiment, one of the two axes of a two dimensional surface area could be scanned by mechanical movement of the object being scanned, perhaps along a track or moving belt. The second scan axis, perpendicular to the mechanically scanned axis, would be provided by tilting the cyclone orifice. This method is useful for minimizing the number of IMS instruments required to fully sample a given surface.

Cyclonic flow when combined with a vacuum may collect particles. The emitted gas flow generally exhibits a quasi-chaotic motion, which may dislodge larger particles from a surface. Once dislodged, the particles may become entrained in the gas flow towards the external sampling orifice. Depending on the application, such particles may or may not be desirable. For example, particles entering the ion source of the IMS may adhere to surfaces and continue to emit vapor for a long period of time, thus causing a continuous erroneous response. A limited range of particle sizes, about 0.5 to 10 micrometers in diameter, may be removed within the tubulation connecting the external sampling orifice to the ion source using electrostatic precipitation. Larger particles tend to be rejected radially outward due to the centrifugal force of the cyclone gas flow. Smaller particles cannot easily be rejected from the sampled gas.

The problem of contamination from particles may also be lessened by heating the tubulation connecting the external gas sample orifice to the ion source. The ion source may also be heated. Heating causes more rapid vaporization or sublimation of the contamination particles, thus shortening the time period of vapor emission and more rapidly cleansing the gas sampling system. As an alternate embodiment, the tubulation 11 may be designed to be an expendable component that is easily removed for cleaning or replacement.

Another advantage of the cyclone gas sampling method for explosive detection is that the system is light in weight, which is important for handheld sampling devices. Compared to existing sampling methods, one or more extra gas pumps are needed, but the power requirements are only a few Watts or less for most applications. An extra pump may also serve other functions in the explosive detection system, such as drawing cooling air from over a heated surface.

Figure 8:
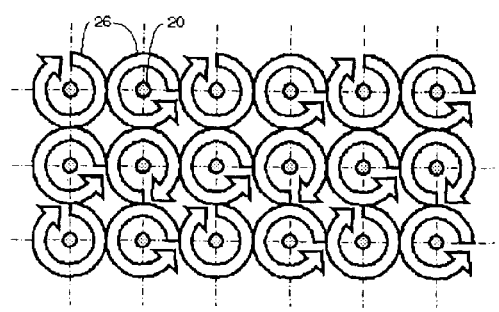
FIG. 8 shows an embodiment of a cyclone nozzle that may be scanned on at least one axis.

The cyclone sampling system may be utilized singly or by means of a plurality of cyclone sampling systems. The external gas orifice may be a single tubulation connected to a single ion source and IMS or there may be tubular branches leading from a single ion source to greater than one cyclone sampling system. Alternately, multiple ion sources plus IMS's plus cyclone sampling systems may be disposed proximally in order to more efficiently sample a larger surface area in a shorter period of time. FIG. 8 shows one possible layout of a plurality of IMS instruments (explosive detection systems). In this case a two dimensional grid is used in which the crossing points of the centering lines 27 is the location of an IMS instrument. The external gas sampling orifice 20 is indicated for each instrument. The circular direction of cyclone gas flow 26 is also indicated as preferably alternating clockwise and counterclockwise for neighboring instruments in order for the neighboring gas flows 26 to always be in the same direction.

When cyclone sampling systems are disposed proximally, neighboring cyclones preferably have rotational directions of the cyclonic gas flow that are oppositely oriented in order not to have the gas flows cancel each other at the boundary.

The gas flow of the gas emitted into the cyclone may be deflected into a circular flow by several possible means. Fractions of the total emitted gas flow may be selectively deflected by means of individually oriented vanes, such that the net resulting gas flow is circular. Alternatively, a hollow cone or cylinder may be employed with a gas flow entering the cone or cylinder at a tangential angle. The inside walls of the hollow cone or cylinder then act as the deflector, constraining the gas flow along a circular path while within the confines of the hollow cone or cylinder. When the emitted gas expands beyond the hollow cone or cylinder, the partial vacuum of the external sampling gas orifice provides the force required to constrain the emitted gas flow from moving tangentially away from the central axis.

Figure 9:
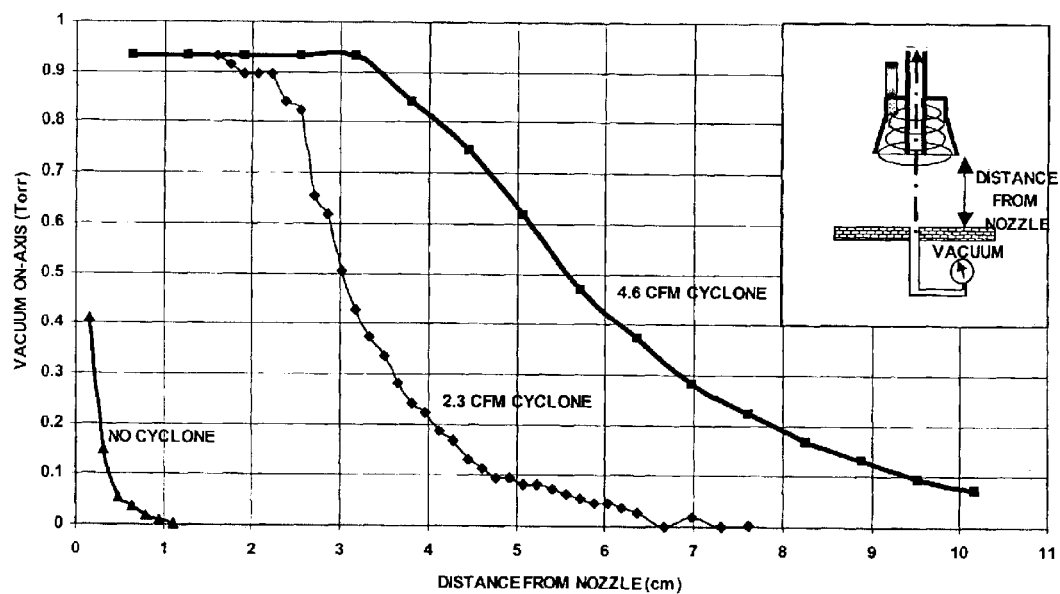
FIG. 9 shows partial vacuum measured on an axis of an external gas sampling orifice for no cyclone, for a 0.6 Watt cyclone with 2.3 cfm air flow, and for a 1.2 Watt cyclone with 4.6 cfm air flow.

FIG. 9 shows the measured vacuum below ambient gas pressure for three different flow rates of the cyclone gas. The external sampling gas orifice is 1.6 centimeters in diameter, and the greatest possible value for vacuum for the gas pump used in this measurement is about 1 Torr (1 millimeter of mercury) less than the ambient gas pressure. When no cyclone flow is present, 10% of maximum vacuum (0.1 Torr) occurs at a distance equal to about 0.25 times the external sampling gas orifice diameter. With a cyclone gas flow equal to 2.3 cubic feet per minute (cfm), the corresponding distance for 10% of maximum vacuum equals about 3.0 times the external sampling gas orifice diameter. With a cyclone gas flow equal to 4.6 cfm, the corresponding distance for 10% of maximum vacuum equals about 5.9 times the external sampling gas orifice diameter. This demonstrates that the length of the virtual extension of the gas sampling tubulation is proportional to the gas flow of the cyclone.

The explosive detection systems described herein may incorporate other novel features, such as features described in copending and commonly assigned U.S. Provisional Application No. 60/357,394, filed Feb. 15, 2002, U.S. Provisional Application No. 60/357,618, filed Feb. 15, 2002, and U.S. Provisional Application No. 60/363,485, filed Mar. 12, 2002.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An explosive detection system, comprising:
    a sampling orifice that receives a sampled gas flow therethrough toward the sampling orifice;
    a fluid rotator that creates a cyclonic gas flow beyond the sampling orifice about the sampled gas flow as the sampled gas flow flows toward the sampling orifice;
    an ion source, coupled to the sampling orifice, that generates ions corresponding to the sampled gas flow;
    a drift tube having the ion source coupled to a first end thereof; and
    a detector coupled to an other end of the drift tube, wherein the detector detects in the sampled gas flow the presence of ions associated with explosives.

2. An explosive detection system, according to claim 1, wherein the cyclonic gas flow has an outer rotary flow about an axis substantially parallel to the central axis of the sampled gas flow and an inner flow substantially parallel to the central axis of the sampled gas flow.

3. An explosive detection system, according to claim 1, wherein the drift tube operates at substantially ambient gas pressure.

4. An explosive detection system, according to claim 1, wherein a gas pump draws a gas flow through the sampling orifice and generates a vacuum within 50 millimeters of mercury (50 Torr) of the substantially ambient gas pressure.

5. An explosive detection system, according to claim 1, wherein the fluid rotator comprises at least one vane.

6. An explosive detection system, according to claim 1, wherein the fluid rotator includes a rotation-inducing orifice surrounding the sampling orifice.

7. An explosive detection system, according to claim 1, wherein the cyclonic gas flow is tilted.

8. An explosive detection system, comprising:
    a sampling orifice that receives sampled gas;
    a fluid rotator that creates a cyclonic gas flow beyond the sampling orifice, wherein the fluid rotator includes a rotation-inducing orifice surrounding the sampling orifice;
    an ion source, coupled to the sampling orifice, that generates ions corresponding to the sampled gas;
    a drift tube having the ion source coupled to a first end thereof; and
    a detector coupled to an other end of the drift tube, wherein the detector detects in the sampled gas the presence of ions associated with explosives, wherein the inside surface of the rotation-inducing orifice deflects a gas flow into a cyclonic gas flow.

9. An explosive detection system, according to claim 8, wherein the cyclonic gas flow has an outer rotary flow about an axis substantially parallel to the central axis of the sampling orifice and an inner flow substantially parallel to the central axis of the sampling orifice.

10. An explosive detection system, according to claim 8, wherein the drift tube operates at substantially ambient gas pressure.

11. An explosive detection system, according to claim 8, wherein a gas pump draws a gas flow through the sampling orifice and generates a vacuum within 50 millimeters of mercury (50 Torr) of the substantially ambient gas pressure.

12. An explosive detection system, according to claim 8, wherein the fluid rotator comprises at least one vane.

13. An explosive detection system, according to claim 8, wherein the fluid rotator includes a rotation-inducing orifice surrounding the sampling orifice.

14. An explosive detection system, according to claim 8, wherein the cyclonic gas flow is tilted.

15. An explosive detection system, comprising:
    a sampling orifice that receives sampled gas;
    a fluid rotator that creates a cyclonic gas flow beyond the sampling orifice, wherein the fluid rotator includes a rotation-inducing orifice surrounding the sampling orifice;
    an ion source, coupled to the sampling orifice, that generates ions corresponding to the sampled gas;
    a drift tube having the ion source coupled to a first end thereof;
    a detector coupled to an other end of the drift tube, wherein the detector detects in the sampled gas the presence of ions associated with explosives; and
    a gas pump connected to the rotation-inducing orifice that creates a cyclonic gas flow.

16. An explosive detection system, according to claim 15, wherein the cyclonic gas flow has an outer rotary flow about an axis substantially parallel to the central axis of the sampling orifice and an inner flow substantially parallel to the central axis of the sampling orifice.

17. An explosive detection system, according to claim 15, wherein the drift tube operates at substantially ambient gas pressure.

18. An explosive detection system, according to claim 15, wherein a gas pump draws a gas flow through the sampling orifice and generates a vacuum within 50 millimeters of mercury (50 Torr) of the substantially ambient gas pressure.

19. An explosive detection system, according to claim 15, wherein the fluid rotator comprises at least one vane.

20. An explosive detection system, according to claim 15, wherein the fluid rotator includes a rotation-inducing orifice surrounding the sampling orifice.

21. An explosive detection system, according to claim 15, wherein the cyclonic gas flow is tilted.

22. An explosive detection system, comprising:
    a sampling orifice that receives sampled gas;
    a fluid rotator that creates a cyclonic gas flow beyond the sampling orifice;
    a drift tube having the ion source coupled to a first end thereof;
    a detector coupled to an other end of the drift tube, wherein the detector detects in the sampled gas the presence of ions associated with explosives; and
    a precipitator that removes at least a portion of any entrained particles within the gas flow into the sampling orifice.

23. An explosive detection system, according to claim 22, wherein the precipitator is an electrostatic precipitator.

24. An explosive detection system, according to claim 23, wherein the electrostatic precipitator includes a cathode disposed on or near the drift tube, the cathode applying a voltage greater than 3000 Volts.

25. An explosive detection system, according to claim 22, wherein the cyclonic gas flow has an outer rotary flow about an axis substantially parallel to the central axis of the sampling orifice and an inner flow substantially parallel to the central axis of the sampling orifice.

26. An explosive detection system, according to claim 22, wherein the drift tube operates at substantially ambient gas pressure.

27. An explosive detection system, according to claim 22, wherein a gas pump draws a gas flow through the sampling orifice and generates a vacuum within 50 millimeters of mercury (50 Torr) of the substantially ambient gas pressure.

28. An explosive detection system, according to claim 22, wherein the fluid rotator comprises at least one vane.

29. An explosive detection system, according to claim 22, wherein the fluid rotator includes a rotation-inducing orifice surrounding the sampling orifice.

30. An explosive detection system, according to claim 22, wherein the cyclonic gas flow is tilted.

31. An explosive detection system, comprising:
   a sampling inlet that receives sampled gas;
   a heat source, mounted proximal to the gas sampling inlet, the heat source providing photonic emissions to one side of a target proximal to the sampling inlet to heat the target while the sampling inlet receives sampled gas;
   an ion source, coupled to the sampling orifice, that generates ions corresponding to the sampled gas;
   a drift tube having the ion source coupled to a first end thereof; and
   a detector coupled to an other end of the drift tube, wherein the detector detects in the sampled gas the presence of ions associated with explosives.

32. An explosive detection system, according to claim 31, wherein the photonic emissions are substantially in the infrared portion of the spectrum.

33. An explosive detection system, according to claim 32, wherein the source of photon emission is made to be substantially in the infrared using at least one of a filter, coating, and covering.

34. An explosive detection system, according to claim 32, wherein the source of photon emission has enhanced emission substantially in the infrared by means of conversion of visible light photons to infrared photons.

35. An explosive detection system, according to claim 31, wherein the photonic emissions are substantially in the combined visible and infrared portion of the spectrum.

36. An explosive detection system, according to claim 31, wherein the photonic emissions are substantially in the visible portion of the spectrum.

37. An explosive detection system, according to claim 36, wherein the source of photon emission is made to be substantially in the visible using at least one of a filter, coating, and covering.

38. An explosive detection system, according to claim 31, wherein the photonic emissions are provided by at least one of a thermally heated surface, a laser, a light emitting diode, and an electrical discharge in a gas.

39. An explosive detection system, according to claim 31, wherein the source of photon emission is at least one of: pulsed, keyed in a long pulse, and continuous.

40. An explosive detection system, according to claim 31, wherein the source of photon emission is separated from the target surface by at least one of a window and a semi-transparent grid.

41. An explosive detection system, according to claim 31, further comprising:
   a precipitator that removes at least a portion of any entrained particles within the gas flow into the sampling inlet.

42. An explosive detection system, according to claim 41, wherein the precipitator is an electrostatic precipitator.

43. An explosive detection system, according to claim 42, wherein the electrostatic precipitator includes a cathode disposed on or near the drift tube, the cathode applying a voltage greater than 3000 Volts.

* * * * *